US012599513B2

(12) United States Patent
Makimura et al.

(10) Patent No.: US 12,599,513 B2
(45) Date of Patent: Apr. 14, 2026

(54) STRETCH LAYERED SHEET, DISPOSABLE WEARING ARTICLE, AND METHOD AND DEVICE FOR MANUFACTURING STRETCH LAYERED SHEET

(71) Applicant: ZUIKO CORPORATION, Osaka (JP)

(72) Inventors: Kazutoshi Makimura, Osaka (JP);
Miwa Koshijima, Osaka (JP)

(73) Assignee: ZUIKO CORPORATION, Osaka (JP)

( * ) Notice: Subject to any disclaimer, the term of this patent is extended or adjusted under 35 U.S.C. 154(b) by 352 days.

(21) Appl. No.: 18/033,862

(22) PCT Filed: Oct. 8, 2021

(86) PCT No.: PCT/JP2021/037345
§ 371 (c)(1),
(2) Date: Apr. 26, 2023

(87) PCT Pub. No.: WO2022/102305
PCT Pub. Date: May 19, 2022

(65) Prior Publication Data
US 2023/0414418 A1      Dec. 28, 2023

(30) Foreign Application Priority Data
Nov. 13, 2020    (JP) ................................. 2020-189437

(51) Int. Cl.
*A61F 13/514*       (2006.01)
*A41D 1/00*       (2018.01)
(Continued)

(52) U.S. Cl.
CPC ............ *A61F 13/5146* (2013.01); *A41D 1/00*
(2013.01); *A41D 31/14* (2019.02);
(Continued)

(58) Field of Classification Search
CPC ................ A61F 13/15699; A61F 13/49; A61F
13/4902; A61F 13/15; A61F 13/15203;
(Continued)

(56) References Cited

U.S. PATENT DOCUMENTS 5,567,501 A      10/1996   Shrinivasan et al.
6,994,761 B2 *    2/2006   Klemp .................. A61F 13/496
156/251

(Continued)

FOREIGN PATENT DOCUMENTS

JP      H06-328600 A      11/1994
JP      2016-189826 A     11/2016
(Continued)

OTHER PUBLICATIONS

International Search Report for corresponding Application No. PCT/JP2021/037345, mailed Dec. 7, 2021.

*Primary Examiner* — Adam Marcetich
(74) *Attorney, Agent, or Firm* — Renner, Otto, Boisselle & Sklar, LLP

(57) ABSTRACT

The present layered stretchable sheet includes: a plurality of attachment portions at which a pair of non-woven fabrics and a film are thermally bonded together, wherein each one of the attachment portions includes at least one thermal bonding area where the pair of non-woven fabrics and the film are thermally bonded together; at least one boundary line that defines the thermal bonding area; a first vent that is defined by a first opening of the film appearing in a stretched state of the film along the boundary line and that exerts air permeability; and a second vent that is defined by a second opening where a part of the film is absent, the second opening being adjacent to the thermal bonding area and (Continued)

being delimited by the boundary line, wherein the second vent exerts air permeability both in the stretched state and in a non-stretched state.

20 Claims, 11 Drawing Sheets

(51) Int. Cl.
| | |
|---|---|
| *A41D 31/14* | (2019.01) |
| *A61F 13/15* | (2006.01) |
| *A61F 13/49* | (2006.01) |
| *A61F 13/51* | (2006.01) |
| *A61F 13/515* | (2006.01) |
| *B29C 65/00* | (2006.01) |
| *B29C 65/08* | (2006.01) |
| *D06C 3/06* | (2006.01) |
| *B29L 31/48* | (2006.01) |

(52) U.S. Cl.
CPC .. *A61F 13/15699* (2013.01); *A61F 13/15764* (2013.01); *A61F 13/49* (2013.01); *A61F 13/515* (2013.01); *B29C 65/08* (2013.01); *B29C 66/344* (2013.01); *B29C 66/45* (2013.01); *B29C 66/7294* (2013.01); *B29C 66/7315* (2013.01); *B29C 66/73182* (2013.01); *B29C 66/8341* (2013.01); *D06C 3/06* (2013.01); *A41D 2500/30* (2013.01); *A61F 2013/15878* (2013.01); *A61F 2013/51026* (2013.01); *B29K 2995/0046* (2013.01); *B29L 2031/4878* (2013.01); *D10B 2509/026* (2013.01)

(58) Field of Classification Search
CPC .......... A61F 13/15682; A61F 13/15707; A61F 13/15764; A61F 13/51; A61F 13/5146; A61F 13/51478; A61F 13/515; A61F 2013/15878; A61F 2013/51026; A61F 2013/51452; B29C 66/344; B29C 66/7294; B29C 65/086; B29C 66/41; B29C 66/81429; B29C 66/81433; B29C 66/83415; B29C 66/83511; B29C 48/08; B32B 27/12; B32B 5/022; B32B 2307/51; B32B 2307/724; B32B 2555/02
See application file for complete search history.

(56) References Cited

U.S. PATENT DOCUMENTS

| | | | | |
|---|---|---|---|---|
| 11,471,549 | B2 * | 10/2022 | Nakagawa | .............. A61L 9/014 |
| 2002/0022426 | A1 * | 2/2002 | Curro | ...................... A47L 13/17 |
| | | | | 442/373 |
| 2003/0180525 | A1 * | 9/2003 | Strack | ............... A61F 13/51464 |
| | | | | 428/323 |
| 2011/0319853 | A1 * | 12/2011 | Yamashita | ............ A61F 13/496 |
| | | | | 604/385.3 |
| 2013/0126070 | A1 * | 5/2013 | Siqueira | .................. B32B 27/32 |
| | | | | 156/229 |
| 2014/0088535 | A1 * | 3/2014 | Xu | ..................... A61F 13/15731 |
| | | | | 604/366 |
| 2015/0360449 | A1 | 12/2015 | Larios et al. | |
| 2017/0087029 | A1 | 3/2017 | Nelson et al. | |
| 2017/0151102 | A1 * | 6/2017 | Isele | ................. A61F 13/51476 |
| 2018/0008481 | A1 | 1/2018 | Takahashi et al. | |
| 2018/0014984 | A1 * | 1/2018 | Sakai | .................... B29C 66/344 |
| 2018/0133357 | A1 * | 5/2018 | Takeda | ............. A61F 13/15203 |
| 2018/0133951 | A1 * | 5/2018 | Takeda | .................. B32B 27/306 |
| 2019/0167487 | A1 * | 6/2019 | Takeuchi | .......... B29C 66/73921 |
| 2019/0254885 | A1 * | 8/2019 | Takeuchi | .......... A61F 13/15739 |
| 2019/0254886 | A1 | 8/2019 | Kokturk et al. | |
| 2019/0374392 | A1 * | 12/2019 | Ninomiya | ......... A61F 13/15699 |
| 2020/0085273 | A1 * | 3/2020 | Izumi | ........................ B32B 3/30 |
| 2020/0197230 | A1 * | 6/2020 | Ohtsubo | ........... A61F 13/15764 |
| 2020/0223195 | A1 * | 7/2020 | Cheng | ..................... B32B 27/34 |
| 2020/0260798 | A1 * | 8/2020 | Morimoto | .............. A41B 9/14 |
| 2020/0375814 | A1 * | 12/2020 | Tsunoda | .................. B32B 33/00 |
| 2022/0087878 | A1 | 3/2022 | Tsunoda | |

FOREIGN PATENT DOCUMENTS

| | | | | |
|---|---|---|---|---|
| JP | 2017-64225 | A | | 4/2017 |
| JP | 2018-51230 | A | | 4/2018 |
| JP | 2019-41887 | A | | 3/2019 |
| JP | 2020-151868 | A | | 9/2020 |
| JP | 7336982 | B2 | * | 9/2023 |

* cited by examiner

FIG. 11A : PRIOR ART     FIG. 11B : PRIOR ART
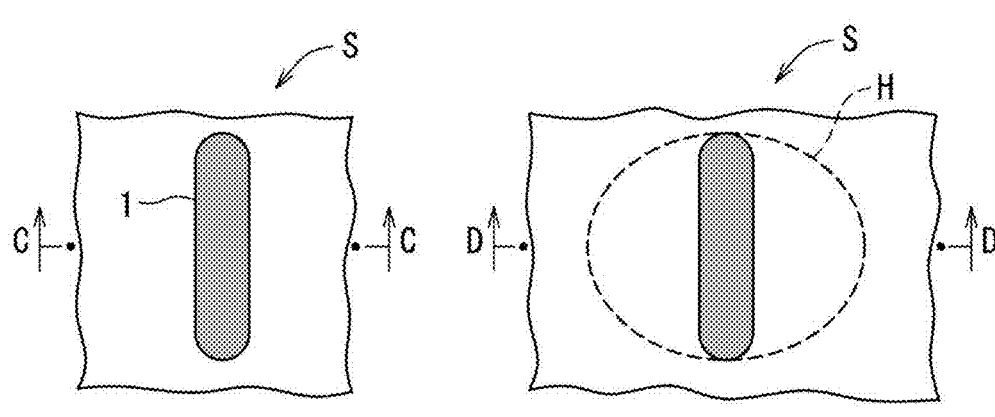
FIG. 11C : PRIOR ART     FIG. 11D : PRIOR ART
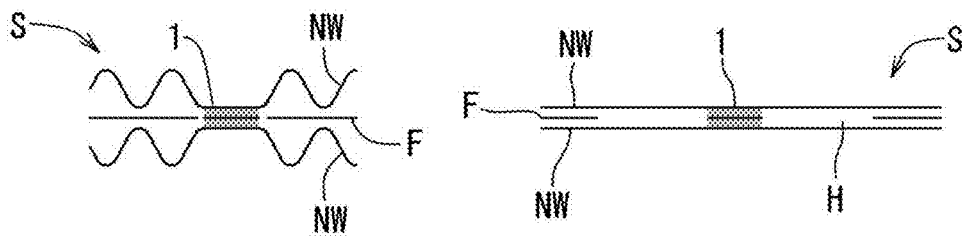

STRETCH LAYERED SHEET, DISPOSABLE WEARING ARTICLE, AND METHOD AND DEVICE FOR MANUFACTURING STRETCH LAYERED SHEET

TECHNICAL FIELD

The present invention relates to a stretchable layered sheet, a disposable worn article, and a method and a device for manufacturing the stretchable layered sheet.

BACKGROUND ART

A stretchable layered sheet having a stretchable film sandwiched between a pair of non-woven fabrics is known in the art (the first patent document). An example of the structure of the sheet is shown in FIG. 11A to FIG. 11D.

FIG. 11A is an enlarged plan view showing the shape of an attachment portion 1 formed in the stretchable layered sheet S, FIG. 11B is an enlarged plan view showing an opening H formed in a film F of the stretchable layered sheet S, FIG. 11C is a cross-sectional view showing a cross section of the stretchable layered sheet S in the non-stretched state, and FIG. 11D is a cross-sectional view showing a cross section of the stretchable layered sheet S in the stretched state.

In FIG. 11A to FIG. 11D, a pair of non-woven fabrics NW, which form a part of the stretchable layered sheet S, include thermoplastic fibers and are air-permeable. On the other hand, the film F, which forms another part of the stretchable layered sheet S, is thermoplastic and is stretchable.

The pair of non-woven fabrics NW and the film F are thermally bonded to each other at the attachment portion 1, which is colored in gray. The periphery of the attachment portion 1 of the film F breaks during thermal bonding or breaks during re-stretching, such as when worn, and an opening H indicated by a dashed line in FIG. 11B appears in the stretched state of the film F shown in FIG. 11B and FIG. 11D. Therefore, in this stretched state, the stretchable layered sheet S exerts air permeability. When such a stretchable layered sheet S is used as the torso portion of the worn article, it suppresses dampness when worn.

CITATION LIST

Patent Document

[FIRST PATENT DOCUMENT] JP2016-189826A (FIG. 3)

SUMMARY OF INVENTION

However, in the non-stretched state in which the stretchable layered sheet S is contracted, the opening H is closed as shown in FIG. 11A and FIG. 11C. Therefore, the air permeability of the stretchable layered sheet S is significantly reduced. Therefore, in the case of a wearer for whom the degree of stretch of the stretchable layered sheet S of the worn article is small, for example, dampness may be caused due to a decrease in air permeability.

Thus, it is an object of the present invention to provide a stretchable layered sheet and a disposable worn article with good air permeability, and also to provide a method and a device for manufacturing such a stretchable layered sheet.

A stretchable layered sheet of the present invention is a stretchable layered sheet including a thermoplastic and stretchable film F layered on at least one sheet of non-woven fabric NW, which includes thermoplastic fibers and is air-permeable, the stretchable layered sheet including:

a plurality of attachment portions 1 at which the non-woven fabric NW and the film F are thermally bonded together, wherein each one of the attachment portions 1 includes at least one thermal bonding area α where the non-woven fabric NW and the film F are thermally bonded together;

at least one boundary line 10 that defines the thermal bonding area α;

a first vent 11 that is defined by a first opening H1 of the film F appearing in a stretched state of the film F along the boundary line 10 and that exerts air permeability; and a second vent 12 that is defined by a second opening H2 where a part of the film F is absent (missing), the second opening H2 being adjacent to the thermal bonding area α and being delimited by the boundary line 10, wherein the second vent 12 exerts air permeability both in the stretched state and in a non-stretched state.

Where there is a pair of non-woven fabrics, the stretchable layered sheet of the present invention is a stretchable layered sheet including a thermoplastic and stretchable film F sandwiched between a pair of non-woven fabrics NW, which includes thermoplastic fibers and is air-permeable, the stretchable layered sheet including:

a plurality of attachment portions 1 at which the pair of non-woven fabrics NW and the film F are thermally bonded together, wherein each one of the attachment portions 1 includes at least one thermal bonding area α where the pair of non-woven fabrics NW and the film F are thermally bonded together;

at least one boundary line 10 that defines the thermal bonding area α;

a first vent 11 that is defined by a first opening H1 of the film F appearing in a stretched state of the film F along the boundary line 10 and that exerts air permeability; and a second vent 12 that is defined by a second opening H2 where a part of the film F is absent (missing), the second opening H2 being adjacent to the thermal bonding area α and being delimited by the boundary line 10, wherein the second vent 12 exerts air permeability both in the stretched state and in a non-stretched state.

The disposable worn article of the present invention is a disposable worn article including the stretchable layered sheet, including:

an around-torso portion that is formed by the stretchable layered sheet, extending in an around-torso direction of a wearer, and configured to cover a torso of the wearer; and an absorbent body configured to cover a crotch of the wearer.

In these sheets and articles, the first opening H1 appears in the stretched state, whereby the first vent 11 exerts air permeability through the pair of non-woven fabrics NW.

On the other hand, in the stretched state and in the non-stretched state (contracted state), the second vent 12 exerts air permeability through the second opening H2 and the pair of non-woven fabrics NW, the second opening H2 being where a part of the film F is absent.

Therefore, the air permeability improves over conventional techniques both in the stretched state and in the non-stretched state.

The manufacturing method of the present invention is a method for manufacturing a stretchable layered sheet including at least one sheet of non-woven fabric NW that includes thermoplastic fibers and is air-permeable, and a thermoplastic and stretchable film F layered thereon, the method including:

a first conveying step of conveying the non-woven fabric NW while stretching the non-woven fabric NW;

a second conveying step of conveying the film F in a stretched state;

a step of layering together the non-woven fabric NW and the film F while performing these conveying steps;

a step of thermally bonding together the non-woven fabric NW and the film F, which have been layered together, at a plurality of attachment portions 1, wherein each one of the attachment portions 1 includes at least one thermal bonding area α where the non-woven fabric NW and the film F are thermally bonded together;

a step in which a part of the film F in the stretched state breaks due to the thermal bonding along at least one boundary line 10, which defines the thermal bonding area α, thereby forming a first opening H1 in the film F to be a first vent 11 that exerts air permeability in the stretched state; and a step in which a part of the film F that is adjacent to the thermal bonding area α and delimited by the boundary line 10 becomes absent (missing) as a result of the thermal bonding, thereby forming a second opening H2 to be a second vent 12 that exerts air permeability both in the stretched state and in a non-stretched state.

Where there is a pair of non-woven fabrics, the manufacturing method of the present invention is a method for manufacturing a stretchable layered sheet including a pair of non-woven fabrics NW that includes thermoplastic fibers and is air-permeable, and a thermoplastic and stretchable film F sandwiched between the pair of non-woven fabrics NW, the method including:

a conveying step of conveying the pair of non-woven fabrics NW while stretching the pair of non-woven fabrics NW;

a conveying step of conveying the film F in a stretched state;

a step of layering together the pair of non-woven fabrics NW and the film F so that the film F is sandwiched between the pair of non-woven fabrics NW while performing these conveying steps;

a step of thermally bonding together the pair of non-woven fabrics NW and the film F, which have been layered together, at a plurality of attachment portions 1, wherein each one of the attachment portions 1 includes at least one thermal bonding area α where the pair of non-woven fabrics NW and the film F are thermally bonded together;

a step in which a part of the film F in the stretched state breaks due to the thermal bonding along at least one boundary line 10, which defines the thermal bonding area α, thereby forming a first opening H1 in the film F to be a first vent 11 that exerts air permeability in the stretched state; and a step in which a part of the film F that is adjacent to the thermal bonding area α and delimited by the boundary line 10 becomes absent as a result of the thermal bonding, thereby forming a second opening H2 to be a second vent 12 that exerts air permeability both in the stretched state and in a non-stretched state.

With the present method, when the non-woven fabrics NW and the film F are thermally bonded together in the thermal bonding area α, the film F in the stretched state partially breaks due to tension along the boundary line 10, thereby forming the first opening H1. This first opening H1 becomes the first vent 11 that allows for an airflow through the pair of non-woven fabrics NW in the stretched state.

Note that "a part of the film F in the stretched state breaks due to the thermal bonding" refers to a case where a part of the film F around the attachment portion 1 breaks during thermal bonding, and also means that there may be a case where the film F breaks when the film F is re-stretched after thermal bonding.

On the other hand, a part of the film F that is adjacent to the thermal bonding area α and delimited by the boundary line 10 becomes absent due to thermal bonding or the breakage, thereby forming the second opening H2. This second opening H2 becomes the second vent 12 that allows for an airflow through the pair of non-woven fabrics NW both in the stretched state and in the non-stretched state.

Thus, with the stretchable layered sheet manufactured by the present method, the air permeability improves over conventional techniques both in the stretched state and in the non-stretched state.

The manufacturing device of the present invention is a device for manufacturing a stretchable layered sheet including at least one sheet of non-woven fabric NW that includes thermoplastic fibers and is air-permeable, and a thermoplastic and stretchable film F layered between the at least one sheets of non-woven fabric NW, the device including:

an anvil roll R including a plurality of protrusions 4 for thermally bonding together the non-woven fabric NW and the film F at a plurality of attachment portions 1; and a thermal bonding device 5 for thermally bonding together the non-woven fabric NW and the film F on the protrusions 4 in cooperation with the anvil roll R, wherein:

each one of the protrusions 4 includes:

at least one protruding surface β corresponding to an area of the attachment portion 1 where thermal bonding occurs;

an edge line 40 that defines the at least one protruding surface β and forms a first opening H1 of the film F, which appears in a stretched state of the film F; and a notch 42 formed by notching the protruding surface β delimited by the edge line 40 for forming a second opening H2 where a part of the film F becomes absent as a result of thermal bonding.

Where there is a pair of non-woven fabrics, the manufacturing device of the present invention is a device for manufacturing a stretchable layered sheet including a pair of non-woven fabrics NW that includes thermoplastic fibers and is air-permeable, and a thermoplastic and stretchable film F sandwiched between the pair of non-woven fabrics NW, the device including:

an anvil roll R including a plurality of protrusions 4 for thermally bonding together the pair of non-woven fabrics NW and the film F at a plurality of attachment portions 1; and a thermal bonding device 5 for thermally bonding together the non-woven fabric NW and the film F on the protrusions 4 in cooperation with the anvil roll R, wherein:

each one of the protrusions 4 includes:

at least one protruding surface β corresponding to an area of the attachment portion 1 where thermal bonding occurs;

an edge line 40 that defines the at least one protruding surface β and forms a first opening H1 of the film F, which appears in a stretched state of the film F; and a notch 42 formed by notching the protruding surface β delimited by the edge line 40 for forming a second opening H2 where a part of the film F becomes absent as a result of thermal bonding.

With the present manufacturing device, the thermal bonding device 5 comes into contact with the protrusions 4 with the non-woven fabrics NW and the film F therebetween, and the non-woven fabrics NW and the film F on the protrusions 4 are heated, thereby thermally bonding together the non-woven fabrics NW and the film F on the protruding surfaces β. In this process, the film F remains in the stretched state, thereby breaking the film F along the edge line 40 of the protruding surface β, and forming the first opening H1.

On the other hand, the notch 42 is provided on the protruding surface β, and a part of the film F in the notch 42 becomes absent due to softening or the breakage caused by the heat generated when the first opening H1 is formed, thus forming the second opening H2 in the film F. The second opening H2 appears also in the non-stretched state of the film F.

Therefore, the air permeability improves over conventional techniques as described above.

BRIEF DESCRIPTION OF THE DRAWINGS

FIG. 3A and FIG. 3B show a torso portion, which is an example of the sheet, in the non-stretched state, wherein FIG. 3A is a plan view showing the torso portion, and FIG. 3B is a plan view showing a part of the torso portion on an enlarged scale.

FIG. 5A to FIG. 5D are super enlarged views of the sheet in the stretched state in which the sheet is stretched in the longitudinal direction, wherein FIG. 5A is a plan view of the sheet, and FIG. 5B, FIG. 50 and FIG. 5D are cross-sectional views taken along line B-B, line C-C and line D-D in FIG. 5A, respectively.

FIG. 7A to FIG. 7D are super enlarged views of the sheet in the non-stretched state, wherein FIG. 7A is a plan view of the sheet, and FIG. 7B, FIG. 7C and FIG. 7D are cross-sectional views taken along line B-B, line C-C and line D-D in FIG. 7A, respectively.

FIG. 10A to FIG. 10D are ultra-expanded views of the stretchable layered sheet in the stretched state where the sheet is stretched in the longitudinal direction when there is one sheet of non-woven fabric, wherein FIG. 10A is a plan view of the sheet, and FIG. 10B, FIG. 100 and FIG. 10D are cross-sectional views of the sheet taken along line B-B, line C-C and line D-D in FIG. 10A, respectively.

FIG. 11A to FIG. 11D are enlarged views showing a part of a conventional stretchable layered sheet, wherein FIG. 11A and FIG. 11B are plan views of the sheet, and FIG. 110 and FIG. 11D are cross-sectional views of the sheet.

In FIG. 3B, FIG. 4, FIG. 5A, FIG. 5B, FIG. 5D, FIG. 6, FIG. 7A, FIG. 7B, FIG. 7D, FIG. 9A to FIG. 9H, FIG. 10A to FIG. 10D, and FIG. 11A to FIG. 11D, thermal bonding areas are colored in gray. In FIG. 5A and FIG. 7A, etc., the boundary of the second opening H2 is indicated by a short dashed line.

DESCRIPTION OF EMBODIMENTS

Figure 1A:
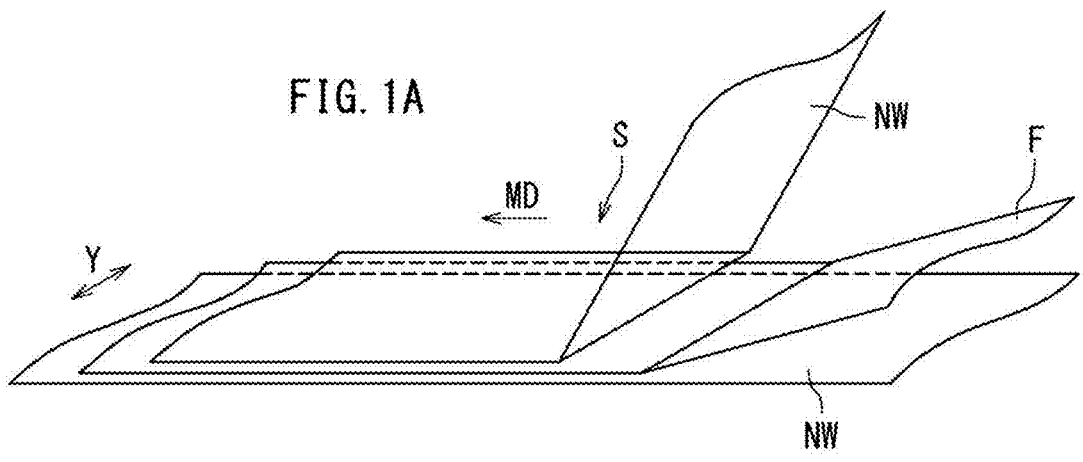
FIG. 1A is a schematic perspective view showing the macroscopic structure of a stretchable layered sheet.

The present invention will be understood more clearly from the following description of preferred embodiments taken in conjunction with the accompanying drawings. Note however that the embodiments and the drawings are merely illustrative and should not be taken to define the scope of the present invention. The scope of the present invention shall be defined only by the appended claims. In the accompanying drawings, like reference numerals denote like components throughout the plurality of figures.

An embodiment of the present invention will now be described.

FIG. 1A to FIG. 9B show Embodiment 1 of the present invention.

The present stretchable layered sheet can be used in various applications. A case where the present stretchable layered sheet is applied to a disposable diaper (an example of a worn article) will now be illustrated. The diaper includes an around-torso portion covering the torso of the wearer and a crotch portion covering the crotch of the wearer. The stretchable layered sheet is used for the around-torso portion.

A more detailed structure used when a stretchable layered sheet is used in a disposable diaper is disclosed, for example, in US 2013/0110073 A1 (WO 2012/017817 A1), the entire disclosure of which is hereby incorporated.

As shown in FIG. 1A, the stretchable layered sheet S is formed by a thermoplastic and stretchable film F sandwiched between a pair of air-permeable non-woven fabrics NW including thermoplastic fibers.

Figures 3A, 3B:
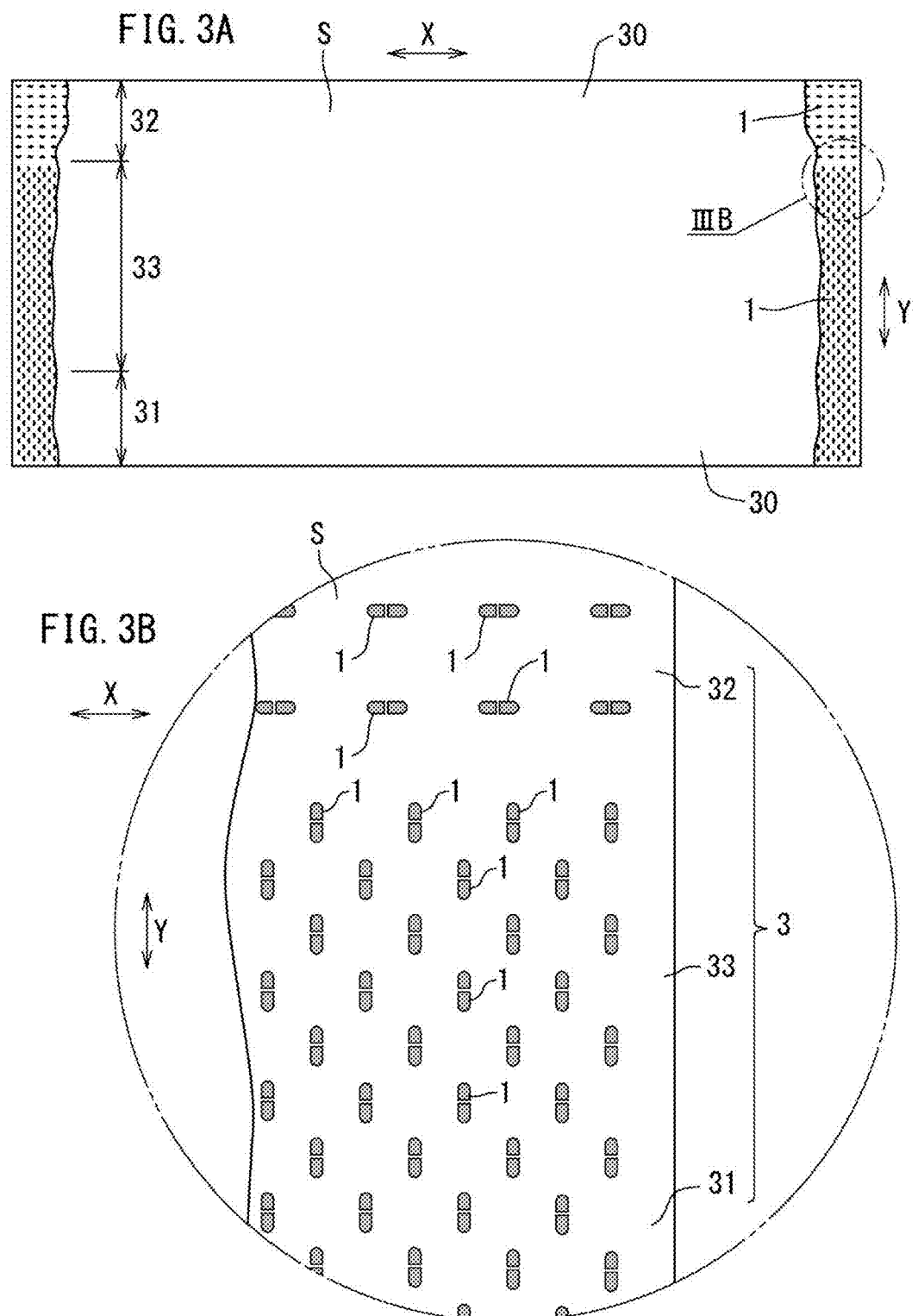

The pair of non-woven fabrics NW and the film F are layered by being thermally bonded to each other at a large number of attachment portions 1 shown in FIG. 3A and FIG. 3B. The stretchable layered sheet S can be used for the flap or the around-torso portion of a disposable diaper, for example. In such a case, the around-torso direction X is the stretch direction in which the stretchable layered sheet S is stretchable.

The attachment portions 1 may be formed by vibration energy of an ultrasonic horn or by heating to an elevated temperature.

An example of a worn article will be described prior to the detailed description of the present stretchable layered sheet.

Figures 2A, 2B:
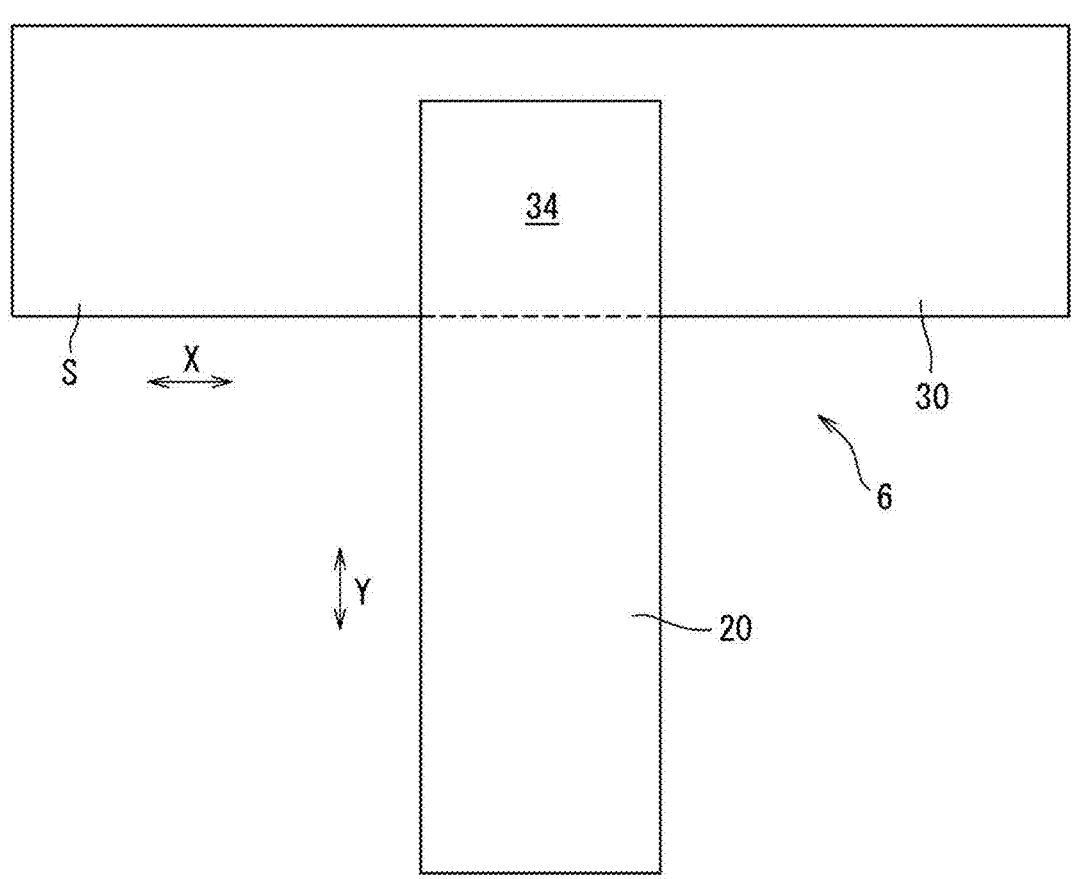
FIG. 2A and FIG. 2B are schematic plan views of a worn article shown in the stretched state.

FIG. 2A and FIG. 2B show a worn article 6.

As shown in these figures, the worn article 6 includes an absorbent body 20 and an around-torso portion 803. The absorbent body 20 is long in the longitudinal direction Y, which is perpendicular to the around-torso direction X. The worn article may be of a diaper type as shown in FIG. 2A or of a pants type as shown in FIG. 2B.

The absorbent body 20 is provided with an absorbent core (not shown). The absorbent core absorbs body fluids. The absorbent core is sandwiched between a top sheet and a back sheet. These sheets and the absorbent core are layered together.

The top sheet is made of a liquid-permeable, thin, non-woven fabric and covers the skin-contact surface of the absorbent core. Cuffs (not shown) may be provided on the top sheet.

The back sheet covers the non-skin-contact surface of the absorbent core and is made of a liquid-impermeable resin sheet. The around-torso portion 30 is bonded to the end portion of the absorbent body 20 in the longitudinal direction Y. That is, the around-torso portion 30 has an overlap 34 that overlaps with the absorbent body 20.

The around-torso portion 30 is formed by the stretchable layered sheet S and is configured to extend in the around-torso direction X of the wearer to cover the torso of the wearer. The absorbent body 20 is configured to cover the crotch of the wearer.

FIG. 3A and FIG. 3B show examples of the stretchable layered sheet S forming the around-torso portion 30.

Horizontal attachment portions 1 are provided in multiple rows and multiple columns (in a matrix) in an upper edge portion 32 of the around-torso portion 30. Vertical attachment portions 1 are provided in multiple rows and multiple columns (in a matrix) in a lower edge portion 31 and a middle portion 33 of the around-torso portion 30. The attachment portions 1 are intermittently arranged in the around-torso portion X and intermittently arranged in the longitudinal direction Y.

The middle portion 33 is the portion between the lower edge portion 31 and the upper edge portion 32, excluding the lower edge portion 31 and the upper edge portion 32. Typically, the upper edge portion 32 is referred to as the waist portion, and the lower edge portion 31 and the middle portion 33 are referred to as the hip portion.

Next, the details of the structure of the stretchable layered sheet S will now be described using the hip portion as an example.

Figures 5A, 5B, 5C, 5D:
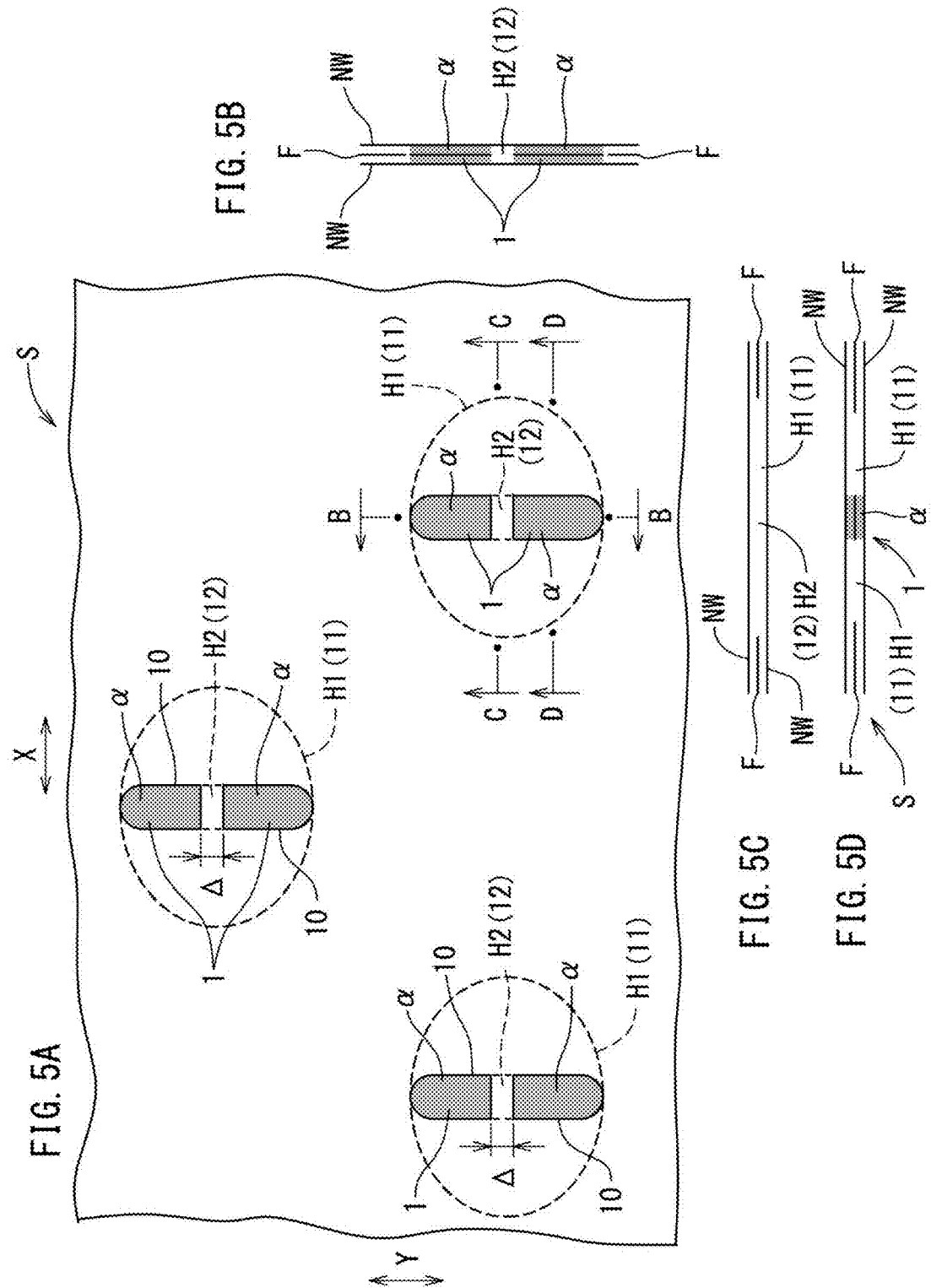
Figure 6:
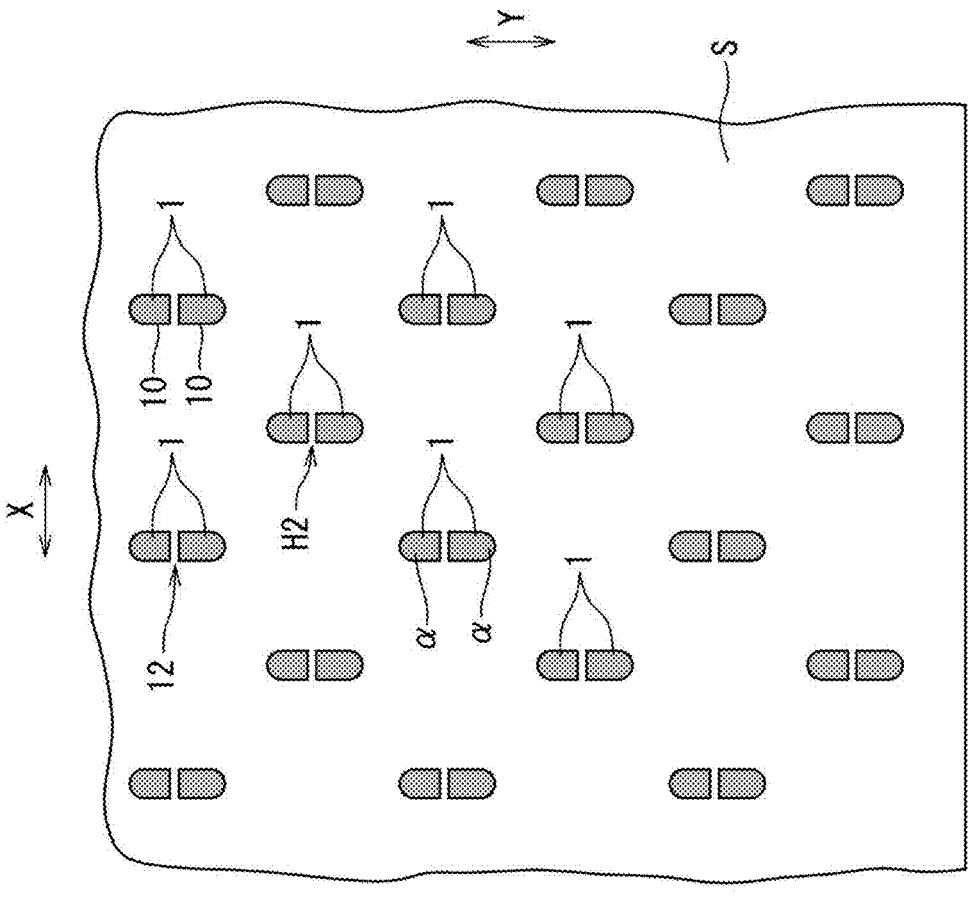
FIG. 6 is an enlarged plan view showing a part of the sheet in the non-stretched state.

As shown in FIG. 5A, each one of the attachment portions 1 includes two thermal bonding areas α, for example, where a pair of non-woven fabrics and a film are thermally bonded to each other. In these figures, the thermal bonding areas α are colored in gray. Each thermal bonding area α is defined by one looped boundary line 10. The boundary line 10 is drawn as a solid line.

As shown in the super enlarged view of FIG. 5A, the stretchable layered sheet S is provided with a first vent 11 and a second vent 12. In FIG. 5A, these vents 11 and 12 are indicated by dashed lines.

The first vent 11 is defined by the first opening H1 of the film F and exerts air permeability. The first opening H1 appears as the boundary line 10 opens as indicated by a dashed line in the stretched state of the film F.

Figures 7A, 7B, 7C, 7D:
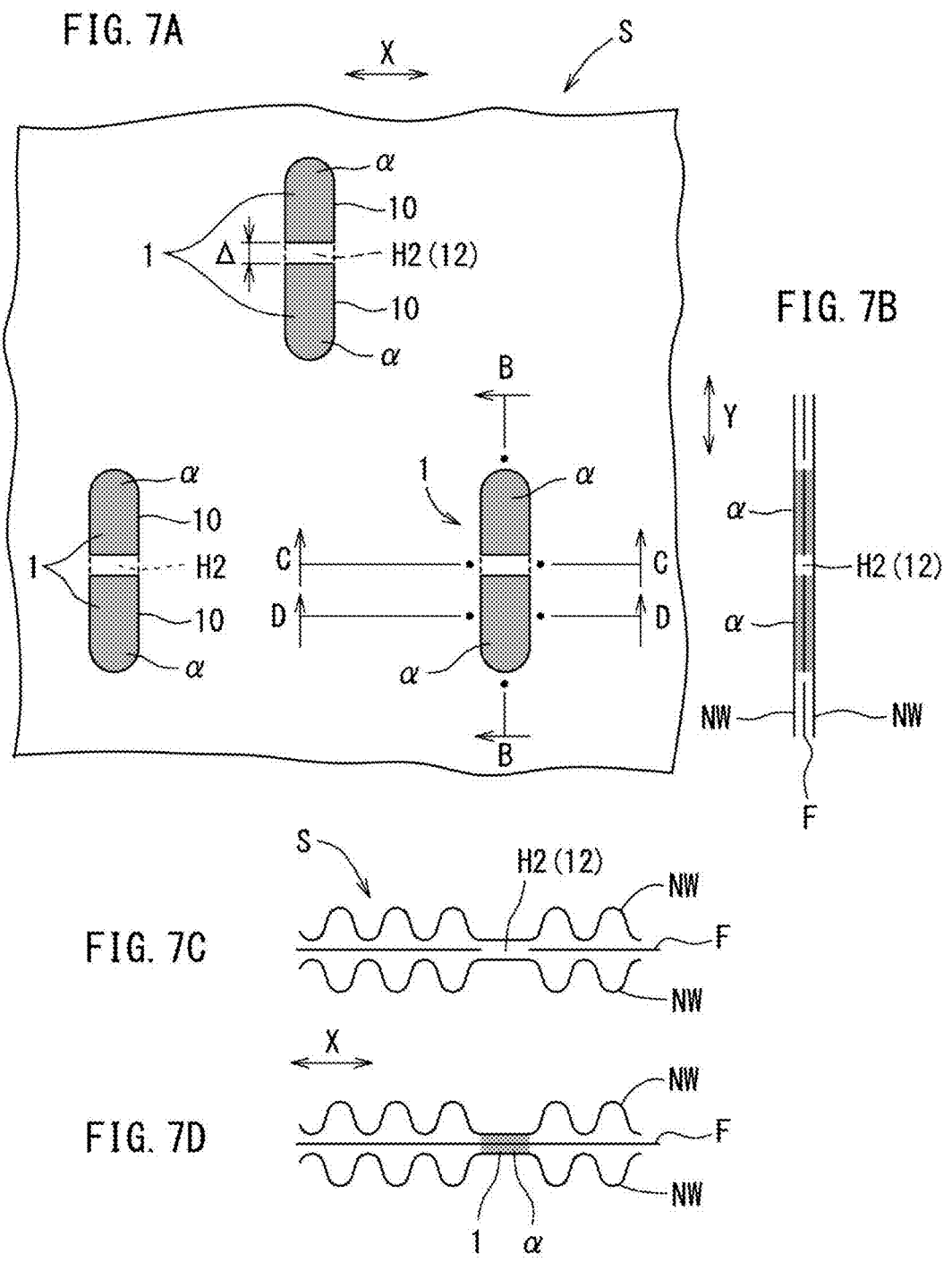

On the other hand, the second vent 12 is adjacent to the thermal bonding area α, delimited by the boundary line 10, and defined by the second opening H2 where a part of the film F is absent, and exerts air permeability both in the stretched state of FIG. 5A and in the non-stretched state of FIG. 7A.

In FIG. 7A, a pair of thermal bonding areas α of each attachment portion 1 are close to each other. The second vent 12 is formed between the thermal bonding areas α. The distance Δ between the two thermal bonding areas α that are close to each other is preferably greater than 0 mm and less than or equal to 3 mm, and more preferably less than or equal to 2 mm.

Figure 4:
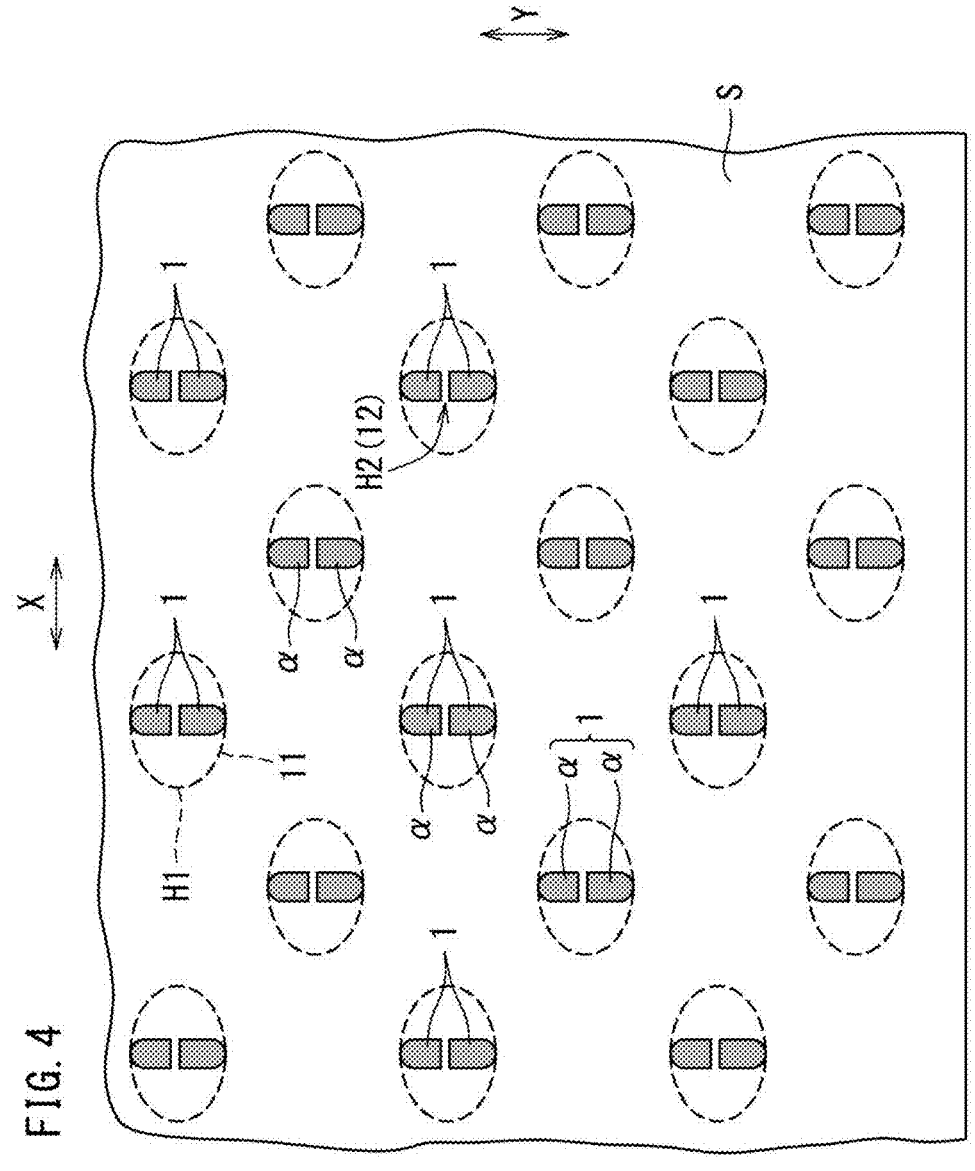
FIG. 4 is an enlarged plan view showing a part of the sheet in the stretched state.

When the stretchable layered sheet S is pulled in the around-torso direction X when the worn article of FIG. 2A and FIG. 2B is worn, the stretchable layered sheet S is stretched in the around-torso direction X. Then, as shown in FIG. 4 and FIG. 5A, the stretchable film F between the pair of non-woven fabrics NW of FIG. 5C and FIG. 5D is easily stretchable in the around-torso direction X and openable in portions of the border line 10 that extend along the edge of the attachment portion 1 perpendicular to the around-torso direction X. Therefore, a large first opening H1 is formed in the stretchable film F as indicated by the dashed line of FIG. 5A. That is, the pulling does not form an opening in the pair of non-woven fabrics NW, which are strong, but the first opening H1 is formed only in the stretchable film F sandwiched between the pair of non-woven fabrics NW.

Figure 1B:
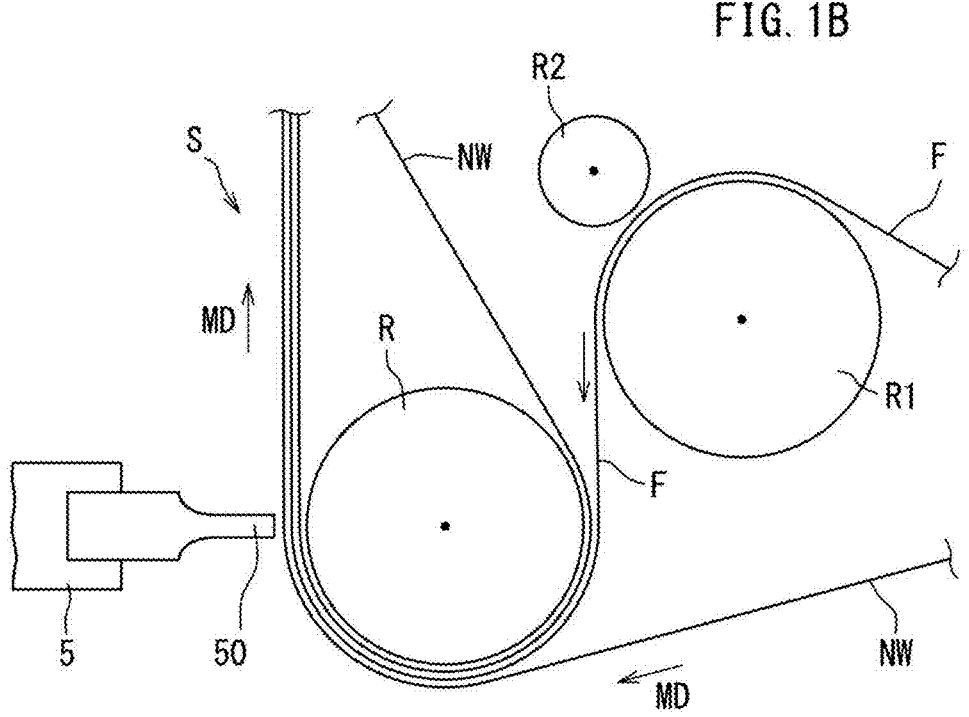
FIG. 1B is a schematic front view showing a device for manufacturing the sheet.

FIG. 1B shows an example of a device for manufacturing the stretchable layered sheet S.

Figures 8A, 8B:
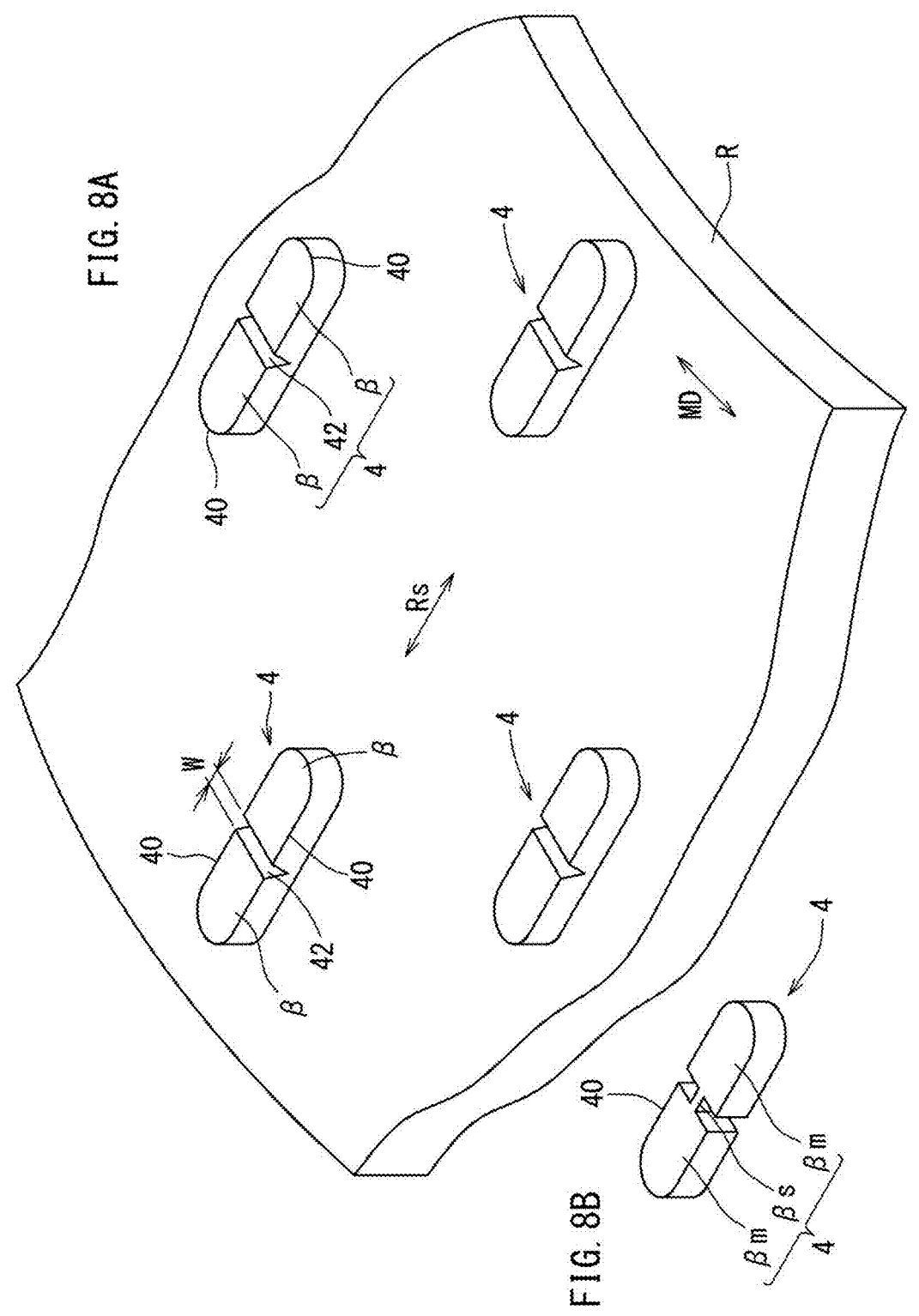
FIG. 8A is an enlarged perspective view showing a part of an anvil roll.
FIG. 8B is an enlarged perspective view showing another example of a protrusion different from a protrusion of FIG. 8A.

In FIG. 1B, the film F is sandwiched between a pair of nip rolls R1, R2 and fed from between the nip rolls R1, R2 toward an anvil roll R. On the other hand, the pair of non-woven fabrics NW are wrapped around the anvil roll R so as to sandwich the film F. A vibration energy from an ultrasonic horn 50 is applied to the three sheet-like materials NW, F layered together. On the surface of the anvil roll R, protrusions 4 of the shape and arrangement matching with the thermal bonding pattern of FIG. 4 are formed as shown in FIG. 8A, and the sheet-like materials NW, F are thermally-bonded (sealed) together at the protrusions 4.

The film F of FIG. 1B is layered on the non-woven fabrics NW in the stretched state with tension applied by the nip rolls R1, R2. When tension is applied to the film F of FIG. 1A, the film F contracts (necks in) in the width direction, which is the longitudinal direction Y of the around-torso portion. Therefore, it is preferable to apply tension to the film F immediately before the film is thermally-bonded together. Thus, as shown in FIG. 1B, it is preferable to arrange a pair of nip rolls R1, R2 upstream of the vicinity of the ultrasonic horn 50 and the anvil roll R.

The ultrasonic horn 50 of FIG. 1B is the output section of a thermal bonding device 5, which in cooperation with the anvil roll R applies vibration energy to the three sheet-like materials NW, F in the attachment portions 1 (FIG. 4), thereby thermally bonding the non-woven fabrics NW and the film F to each other. That is, the thermal bonding device 5 of this example is an ultrasonic thermal bonding device that uses ultrasonic energy for the thermal bonding.

Next, the details of the protrusions 4 of FIG. 8A of the anvil roll R will be described.

As shown in FIG. 8A, on the anvil roll R, a large number of protrusions 4 are arranged intermittently in the circumferential direction of the anvil roll R and intermittently in the axial direction Rs of the anvil roll R. The large number of protrusions 4 are provided so as to correspond to the attachment portions 1 (FIG. 4). Note that, for convenience of drawing, only those of the protrusions 4 of FIG. 8A that correspond to the attachment portions 1 of the lower edge portion 31 of the around-torso portion 30 of FIG. 3A are shown in the figure on an enlarged scale, and those that correspond to the upper edge portion 32 of FIG. 3B are not shown.

The protrusions 4 of FIG. 8A each have two protruding surfaces β in this example. The two protruding surfaces β are adjacent to each other with a notch 42 therebetween. These protruding surfaces β correspond to the thermal bonding areas α of FIG. 5A, whereas the notches 42 (FIG. 8A) correspond to the second openings H2.

In FIG. 8A, one protruding surface β is defined by being surrounded by a single loop edge line 40 and forms the first opening H1 of the film F, which appears in the stretched state of the film F of FIG. 5A. The mechanism of this formation will be explained in the description of the manufacturing method below.

Here, it would be preferable for the edge line 40 of FIG. 8A to have a small C-shaped surface or arch, rather than a pointed shape. An appropriately sized C-shaped surface or arch would allow the film F to be fused without damaging the non-woven fabrics NW.

The notch 42 of FIG. 8A is delimited by the edge line 40, i.e., defined between two edge lines 40, 40, and is formed by notching the protruding surface β. This notch 42 produces the second opening H2 of FIG. 7A, where the film F is absent, during the thermal bonding of the film F. The mechanism of this formation will be explained in the description of the manufacturing method below.

Note that the distance Δ of FIG. 7A corresponds to the width W (FIG. 8A) of the notch 42 of FIG. 8A, and is close or equal thereto.

Next, an example of a method for manufacturing a stretchable layered sheet will be described.

As shown in FIG. 1B, continuous sheets of the pair of non-woven fabrics NW are conveyed while being stretched, and the film F is conveyed in the stretched state. These are layered together on the anvil roll R so that the film F is sandwiched between the continuous sheets of the pair of non-woven fabrics NW.

In this process, as is well known in the art, the non-woven fabrics NW are held under such a tension they do not slack, whereas the film F is conveyed on the anvil roll R in the stretched state so as to be contracted later. Note that the film F will later be in the contracted, non-stretched state, but it is preferred to apply a tension on the film F so that the permanent strain of the film F is greater than 0% and less than or equal to about 10%.

When the pair of non-woven fabrics NW and the film F of FIG. 1B pass between the ultrasonic horn 50 and the protrusions 4 (8A) of the anvil roll R, the ultrasonic horn 50 vibrates ultrasonically in the direction toward the anvil roll R. As a result, the non-woven fabrics NW are thermally bonded together with the film F therebetween in the thermal bonding areas α of the attachment portions 1 of FIG. 5A to FIG. 5D, thereby producing the stretchable layered sheet S. During this thermal bonding, the first openings H1 and the second openings H2 are formed in the film F as will be described below.

During the thermal bonding, as described above, a tension is applied to the film F and the film F is in the stretched state. During this thermal bonding, the film F in the attachment portions 1 is heated and softened, and the tension causes portions of the film F to break along the boundary line 10 indicated by the solid line, and oval-shaped first openings H1, for example, appear as indicated by dashed lines. The first opening H1 becomes the first vent 11 when worn and exerts air permeability.

Note that some of the first openings H1 may be once closed after thermal bonding, and may appear again as the film F breaks when the film F is re-stretched, such as when worn. Note that the first openings H1 may appear by performing a stretch process as shown in Japanese National Phase PCT Laid-open Publication No. 2000-513054 after the thermal bonding process.

During the thermal bonding, the first openings H1 are formed and the second openings H2 are formed between the thermal bonding areas α. That is, during the thermal bonding, the film F is pulled in the around-torso direction X as described above, and when the first openings H1 are formed, because the distance between the thermal bonding area α and the thermal bonding area α is small, the area of the film between the thermal bonding area α and the thermal bonding area α is also influenced by heat from both sides during thermal bonding to become absent. For example, it is assumed that this area of the film is pulled in the around-torso direction X and breaks along the boundary line 10, or shrinks in the longitudinal direction Y due to necking and becomes absent. The second openings H2 thus formed become the second vents 12, which exert air permeability both in the stretched state and in the non-stretched state.

After the absorbent body 20 is arranged on the stretchable layered sheet S thus produced, as shown in FIG. 2A, a pants-type worn article 6 is obtained as shown in FIG. 2B, for example. In the worn article 6, the stretched state of the stretchable layered sheet S transitions to the non-stretched state in which no tension is applied in the around-torso direction X.

In the non-stretched state, the first openings H1 of FIG. 5A and FIG. 5D are closed as shown in FIG. 7A and FIG. 7D. In the non-stretched state, gathers appear in the non-woven fabrics NW as shown in FIG. 7C and FIG. 7D as the film F contracts.

Figure 9A:
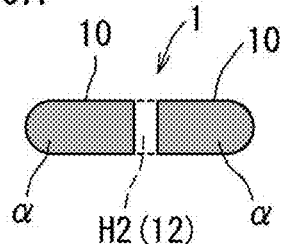
FIG. 9A, FIG. 9B, FIG. 9C, FIG. 9D, FIG. 9E, FIG. 9F, FIG. 9G and FIG. 9H are super enlarged plan views showing other examples of an attachment portion, a first vent and a second vent.
Figure 9B:
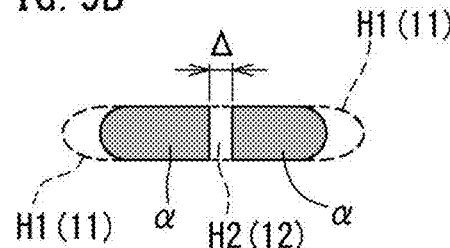

Next, the attachment portions 1 of the upper edge portion 32 of the around-torso portion 30 of FIG. 3B will be briefly described. As shown in FIG. 9A and FIG. 9B, the attachment portion 1 is long in the around-torso portion X, i.e., along the stretch direction of the film. In this case, the first openings H1 are small and the film elongation is also small.

Note that while the second openings H2 of FIG. 9A slightly widen in the stretch direction (the around-torso direction X) in the stretched state of FIG. 9B, the width W in FIG. 9A and the width W in FIG. 9B are shown to be the same for convenience of drawing.

FIG. 9C to FIG. 9H show other examples of the attachment portions 1.

Figure 9C:
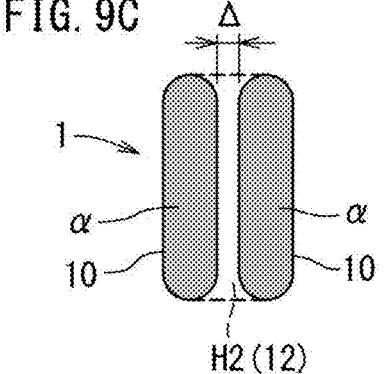
Figure 9D:
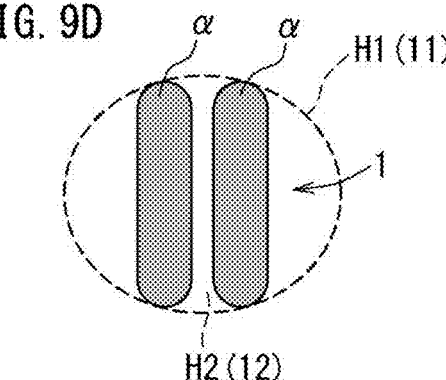

As shown in FIG. 9C and FIG. 9D, the attachment portion 1 may have two long thermal bonding areas α, α spaced apart from each other in the around-torso portion direction X (the stretch direction).

Figure 9E:
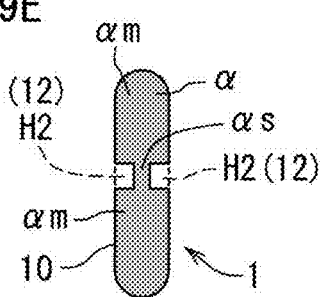
Figure 9F:
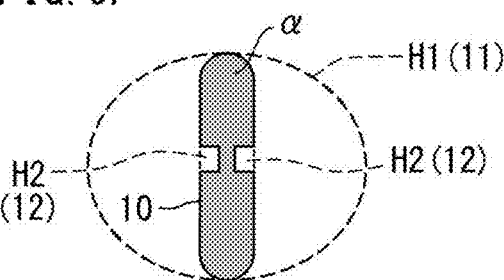

As shown in the examples of FIGS. 9E and 9F, the thermal bonding area α may include a necked narrow portion αs and two main portions αm that are continuous with each other via the narrow portion αs and that are larger than the narrow portion αs. In this case, the second openings H2 are adjacent to the narrow portion αs.

The attachment portion 1 in this example is formed by the protrusion 4 of FIG. 8B. In FIG. 8B, each protruding surface β includes a necked narrow portion βs and two main portions βm that are continuous with each other via the narrow portion βs and that are larger than the narrow portion βs.

In this case, the notch 42 is formed between the two main portions βm.

Figure 9G:
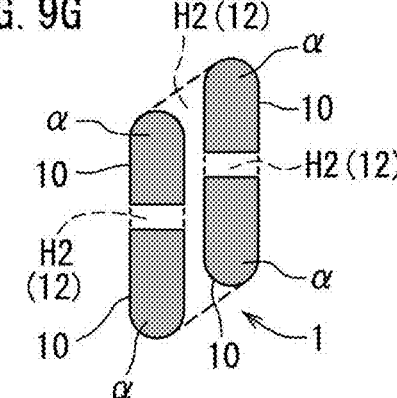
Figure 9H:
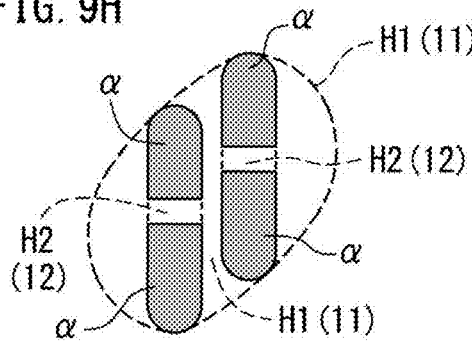

As shown in FIGS. 9G and 9H, one attachment portion 1 may include four thermal bonding areas α. In this case, the thermal bonding areas α are spaced apart from each other in two directions, i.e., the stretch direction of the film and another direction perpendicular thereto.

Next, an example of the stretchable layered sheet S including one non-woven fabric NW and one film F layered together will be described with reference to FIG. 10A to FIG. 10D.

Figures 10A, 10B, 10C, 10D:
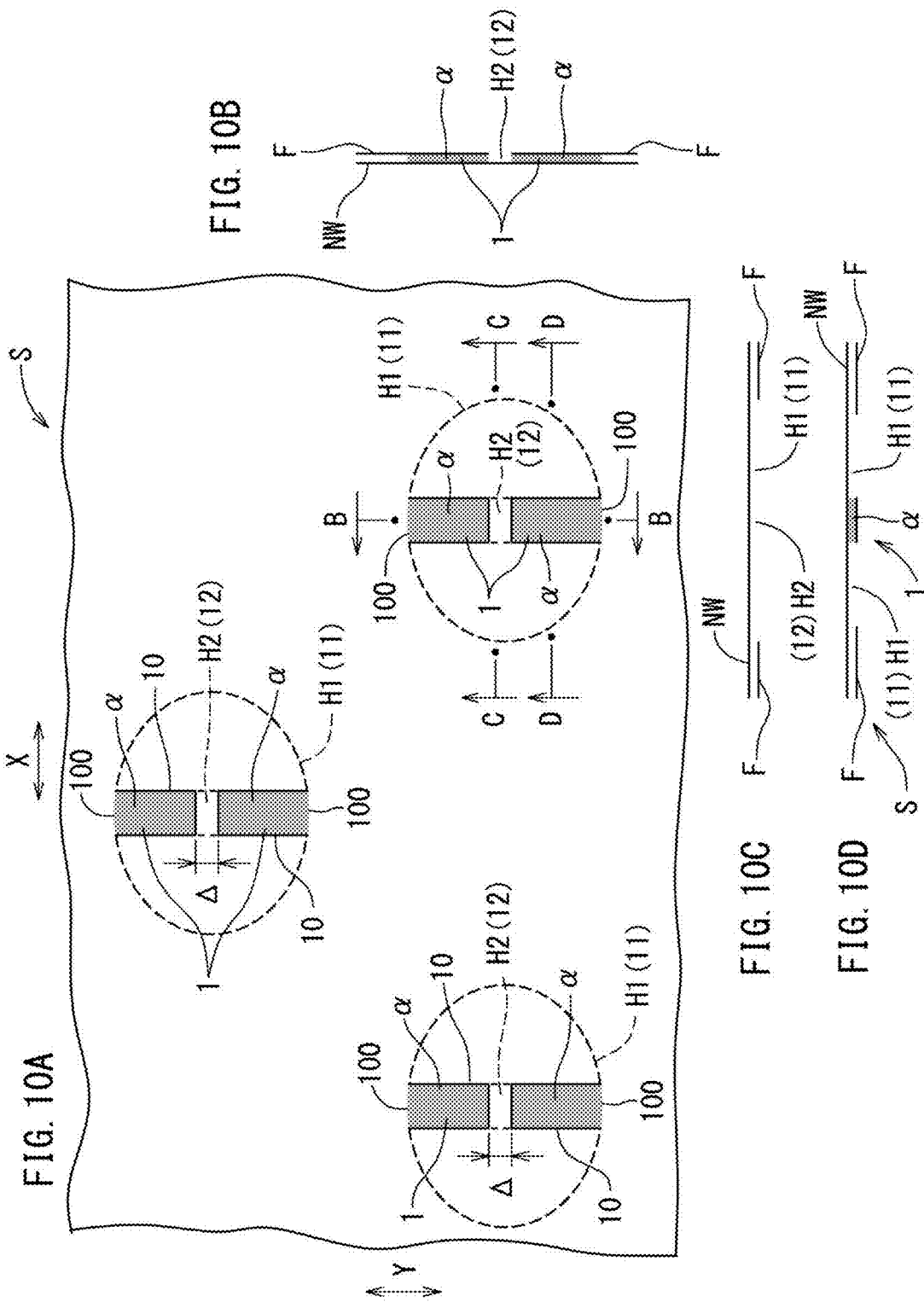

In this case, as shown in FIG. 10A and FIG. 10B, the non-woven fabric NW and the film F may be continuous with each other without the film F being broken at the upper and lower edges 100 of the attachment portions 1. In this case, due to this continuity, it is possible to maintain a state where the non-woven fabric NW and the film F of FIG. 10C and FIG. 10D are layered together.

In order to form such continuous edges 100, one may consider employing a method in which a large arch is formed in a portion of the edge line 40 of FIG. 8A.

The invention conceived from the embodiments described above comprises the following preferred embodiments.

In a preferred embodiment, each attachment portion 1 of a plurality of attachment portions 1 includes a plurality of thermal bonding areas α adjacent to each other; and the second vent 12 is formed between the thermal bonding areas α.

Where the second vent 12 is present between the thermal bonding areas α, it is easy to form the second vent 12.

In a more preferred embodiment, the distance between the thermal bonding areas α adjacent to each other is greater than 0 mm and less than or equal to 3 mm.

If this distance is greater than 3 mm, the film F does not soften, and the second opening H2 is unlikely to be formed, between the thermal bonding areas α.

In a preferred embodiment, a thermal bonding area α includes a necked narrow portion αs and a plurality of main portions αm that are continuous with each other via the narrow portion αs and that are larger than the narrow portion αs; and the second vent 12 is formed between the main portions αm.

In this case, as the thermal bonding area α includes the narrow portion αs, the size of the second vent 12 may become smaller as compared with a case where there are a plurality of thermal bonding areas α. However, it may improve the accuracy of forming the second openings H2.

In a more preferred embodiment, the distance between the main portions αm is greater than 0 mm and less than or equal to 3 mm.

If the distance is greater than 3 mm, the film F does not soften, and the second opening H2 is unlikely to be formed, between the thermal bonding areas α adjacent to each other.

A preferred manufacturing method further includes, after the thermal bonding step, a step of transitioning the stretchable layered sheet from the stretched state to the non-stretched state; and the permanent strain of the film F in the non-stretched state is greater than 0% and less than or equal to 10%.

When the permanent strain is large, the second opening H2 is likely to be formed even if the distance between the thermal bonding areas α is large, but when the permanent strain is too large, the stretchability will be poor. Therefore, it is preferred to balance these factors and set the permanent strain to 0% to 10%.

In a preferred manufacturing method, each protrusion 4 includes a plurality of protruding surfaces β adjacent to each other; and the notch 42 is formed between the protruding surfaces β.

In this case, the film F becomes absent due to heat or tension in the notch 42 during thermal bonding.

In another preferred manufacturing method, each protruding surface β includes a necked narrow portion βs and a plurality of main portions βm that are continuous with each other via the narrow portion βs and that are larger than the narrow portion βs; and the notch 42 is formed between the main portions βm.

In this case, the film F becomes absent due to heat or tension between the main portions βm during thermal bonding.

Any feature illustrated and/or depicted in conjunction with one embodiment or preferred embodiments may be used in the same or similar form in one or more of the other embodiments, and/or may be used in combination with, or in place of, the other embodiments.

While preferred embodiments have been described above with reference to the drawings, obvious variations and modifications will readily occur to those skilled in the art upon reading the present specification.

For example, one or both of the non-woven fabrics NW may be discontinuous non-woven fabrics instead of continuous non-woven fabrics. The non-woven fabrics may be non-stretchable. The non-woven fabrics may be stretchable non-woven fabrics or crimped non-woven fabrics.

Thus, such variations and modifications shall fall within the scope of the present invention as defined by the appended claims.

INDUSTRIAL APPLICABILITY

The stretchable layered sheet of the present invention may be used as a part of a member of a disposable worn article, or the like.

REFERENCE SIGNS LIST

1: Attachment portion, 10: Boundary line
11: First vent, 12: Second vent
20: Absorbent body
30: Around-torso portion, 31: Lower edge portion, 32: Upper edge portion, 33: Middle portion, 34: Overlap
4: Protrusion, 40: Edge line, 42: Notch
5: Thermal bonding device, 50: Ultrasonic horn
6: Worn article
F: Film
NW: Non-woven fabric
H: Opening, H1: First opening, H2: Second opening, MD: Conveyance direction
R: Anvil roll, R1, R2: Nip roll, Rs: Axial direction
S: Stretchable layered sheet
X: Around-torso direction
Y: Longitudinal direction
W: Width
α: Thermal bonding area, αm: Main portion, αs: Narrow portion
β: Protruding surface, βm: Main portion, βs: Narrow portion
Δ: Distance

The invention claimed is:

1. A stretchable layered sheet including a thermoplastic and stretchable film layered on at least one sheet of non-woven fabric, the non-woven fabric including thermoplastic fibers and being air-permeable, the stretchable layered sheet comprising:

a plurality of attachment portions at which the non-woven fabric and the film are thermally bonded together, wherein each one of the attachment portions includes at least one thermal bonding area where the non-woven fabric and the film are thermally bonded together;

at least one boundary line that defines the thermal bonding area, each of the at least one boundary line having associated therewith:

a first vent that is defined by a first opening of the film appearing in a stretched state of the film along the at least one boundary line, the first vent exerting air permeability and a second vent that is defined by a second opening where a part of the film is absent, the second opening being adjacent to the thermal bonding area and being delimited by the at least one boundary line, the second vent exerting air permeability both in the stretched state and in a non-stretched state.

2. The stretchable layered sheet according to claim 1, wherein:

the at least one sheet of non-woven fabric includes a pair of non-woven fabrics;

the film is sandwiched between the pair of non-woven fabrics; and the pair of non-woven fabrics and the film are thermally bonded together in the thermal bonding area of each one of the attachment portions.

3. The stretchable layered sheet according to claim 2, wherein:

each one of the attachment portions includes a plurality of thermal bonding areas of the at least one thermal bonding area, the thermal bonding areas being adjacent to each other; and the second vent is formed between the thermal bonding areas.

4. The stretchable layered sheet according to claim 2, wherein:

the thermal bonding area includes a necked narrow portion and a plurality of main portions that are continuous with each other via the narrow portion and that are larger than the narrow portion; and the second vent is formed between the main portions.

5. A disposable worn article including the stretchable layered sheet according to claim 2, comprising:

an around-torso portion that is formed by the stretchable layered sheet, extending in an around-torso direction of a wearer, and configured to cover a torso of the wearer; and an absorbent body configured to cover a crotch of the wearer.

6. The stretchable layered sheet according to claim 1, wherein:

each one of the attachment portions includes a plurality of thermal bonding areas of the at least one thermal bonding area, the thermal bonding areas being adjacent to each other; and the second vent is formed between the thermal bonding areas.

7. The stretchable layered sheet according to claim 6, wherein a distance between the thermal bonding areas adjacent to each other is greater than 0 mm and less than or equal to 3 mm.

8. The stretchable layered sheet according to claim 1, wherein:

the thermal bonding area includes a necked narrow portion and a plurality of main portions that are continuous with each other via the narrow portion and that are larger than the narrow portion; and the second vent is formed between the main portions.

9. The stretchable layered sheet according to claim 8, wherein a distance between the main portions is greater than 0 mm and less than or equal to 3 mm.

10. A disposable worn article including the stretchable layered sheet according to claim 1, comprising:

an around-torso portion that is formed by the stretchable layered sheet, extending in an around-torso direction of a wearer, and configured to cover a torso of the wearer; and an absorbent body configured to cover a crotch of the wearer.

11. A device for manufacturing a stretchable layered sheet according to claim 1, the device comprising:

an anvil roll including a plurality of protrusions for thermally bonding together the non-woven fabric and the film at a plurality of attachment portions; and a thermal bonding device for thermally bonding together the non-woven fabric and the film on the protrusions in cooperation with the anvil roll, wherein:

each one of the protrusions includes:

at least one protruding surface corresponding to an area of the attachment portion where thermal bonding occurs;

an edge line that defines the at least one protruding surface and forms a first opening of the film, the first opening appearing in a stretched state of the film; and a notch formed by notching the protruding surface delimited by the edge line for forming a second opening where a part of the film becomes absent as a result of thermal bonding.

12. The device for manufacturing a stretchable layered sheet according to claim 11, wherein:

the at least one sheet of non-woven fabric includes a pair of non-woven fabrics, and the film is sandwiched between the pair of non-woven fabrics; and the anvil roll is an anvil roll having the plurality of protrusions for thermally bonding together the pair of non-woven fabrics and the film at the plurality of attachment portions.

13. The device for manufacturing a stretchable layered sheet according to claim 12, wherein:

each protrusion of the protrusions includes a plurality of protruding surface adjacent to each other; and the notch is formed between the protruding surfaces.

14. The device for manufacturing a stretchable layered sheet according to claim 12, wherein:

each protruding surface of the at least one protruding surface includes a necked narrow portion and a plurality of main portions, the main portions being continuous with each other via the narrow portion and being larger than the narrow portion; and the notch is formed between the main portions.

15. The device for manufacturing a stretchable layered sheet according to claim 11, wherein:

each protrusion of the protrusions includes a plurality of protruding surface adjacent to each other; and the notch is formed between the protruding surfaces.

16. The device for manufacturing a stretchable layered sheet according to claim 11, wherein:

each protruding surface of the at least one protruding surface includes a necked narrow portion and a plurality of main portions, the main portions being continuous with each other via the narrow portion and being larger than the narrow portion; and the notch is formed between the main portions.

17. A method for manufacturing a stretchable layered sheet comprising at least one sheet of non-woven fabric that includes thermoplastic fibers and is air-permeable, and a thermoplastic and stretchable film layered on the non-woven fabric, the method comprising:

a first conveying step of conveying the non-woven fabric while stretching the non-woven fabric;

a second conveying step of conveying the film in a stretched state;

a step of layering together the non-woven fabric and the film while performing the first and second conveying steps;

a step of thermally bonding together the non-woven fabric and the film, which have been layered together, at a plurality of attachment portions, wherein each one of the attachment portions includes at least one thermal bonding area a where the non-woven fabric and the film are thermally bonded together;

a step in which a part of the film in the stretched state breaks due to the thermal bonding along at least one boundary line, which defines the thermal bonding area, thereby forming a first opening in the film to be a first vent that exerts air permeability in the stretched state; and a step in which a part of the film that is adjacent to the thermal bonding area and delimited by the at least one boundary line becomes absent as a result of the thermal bonding, thereby forming a second opening to be a second vent that exerts air permeability both in the stretched state and in a non-stretched state, the first opening and the second opening provided for each of the at least one boundary line that defines the thermal bonding area.

18. The method for manufacturing a stretchable layered sheet according to claim 17, wherein:

the at least one sheet of non-woven fabric includes a pair of non-woven fabrics, and the film is sandwiched between the pair of non-woven fabrics;

in the first conveying step, the pair of non-woven fabrics are conveyed while being stretched;

in the layering step, the pair of non-woven fabrics and the film are layered together so that the film is sandwiched between the pair of non-woven fabrics while the first and second conveying steps are performed; and in the thermal bonding step, the pair of non-woven fabrics and the film are thermally bonded together at the plurality of attachment portions, and the pair of non-woven fabrics and the film are thermally bonded together in the thermal bonding area of the attachment portions.

19. The method for manufacturing a stretchable layered sheet according to claim 18, further comprising:

after the thermal bonding step, a step of transitioning the stretchable layered sheet from the stretched state to the non-stretched state, wherein:

a permanent strain of the film in the non-stretched state is greater than 0% and less than or equal to 10%.

20. The method for manufacturing a stretchable layered sheet according to claim 17, further comprising:

after the thermal bonding step, a step of transitioning the stretchable layered sheet from the stretched state to the non-stretched state, wherein:

a permanent strain of the film in the non-stretched state is greater than 0% and less than or equal to 10%.

* * * * *